(12) United States Patent
Xia et al.

(10) Patent No.: US 9,169,186 B2
(45) Date of Patent: Oct. 27, 2015

(54) SYSTEM AND METHOD FOR CONTINUOUSLY PRODUCING POLYOXYMETHYLENE DIMETHYL ETHERS

(71) Applicant: Lanzhou Institute of Chemical Physics, Chinese Academy of Sciences, Lanzhou (CN)

(72) Inventors: Chungu Xia, Lanzhou (CN); Heyuan Song, Lanzhou (CN); Jing Chen, Lanzhou (CN); Fuxiang Jin, Lanzhou (CN); Meirong Kang, Lanzhou (CN)

(73) Assignee: Lanzhou Institute of Chemicals Physics, Chinese Academy of Sciences, Lanzhou (CN)

( * ) Notice: Subject to any disclaimer, the term of this patent is extended or adjusted under 35 U.S.C. 154(b) by 253 days.

(21) Appl. No.: 13/723,146

(22) Filed: Dec. 20, 2012

(65) Prior Publication Data

US 2014/0114092 A1     Apr. 24, 2014

(30) Foreign Application Priority Data

Oct. 18, 2012   (CN) .......................... 2012 1 0397887

(51) Int. Cl.
| | |
|---|---|
| *C07C 41/50* | (2006.01) |
| *C07C 41/56* | (2006.01) |
| *C07C 41/60* | (2006.01) |
| *B01J 14/00* | (2006.01) |
| *C07C 41/58* | (2006.01) |

(52) U.S. Cl.
CPC ................. *C07C 41/58* (2013.01); *B01J 14/00* (2013.01); *C07C 41/50* (2013.01); *C07C 41/56* (2013.01); *C07C 41/60* (2013.01)

(58) Field of Classification Search
None
See application file for complete search history.

(56) References Cited

U.S. PATENT DOCUMENTS

| | | | |
|---|---|---|---|
| 6,534,685 | B1 | 3/2003 | Patrini et al. |
| 7,235,113 | B2 | 6/2007 | Sanfilippo et al. |

(Continued)

FOREIGN PATENT DOCUMENTS

| | | |
|---|---|---|
| CA | 2581502 A1 | 5/2006 |
| CN | 101665414 A | 3/2010 |

(Continued)

*Primary Examiner* — Jennifer A Leung
(74) *Attorney, Agent, or Firm* — Manni Li; Mei & Mark LLP (57) ABSTRACT

A system and method for producing polyoxymethylene dimethyl ethers ($DMM_n$) using an aqueous formaldehyde solution as the initial reaction material. The process system has a polymerization reaction unit, an acetalation unit, a product separation unit, and a catalyst regeneration unit. Both polymerization and acetalation reaction are conducted in the presence of an ionic liquid as a catalyst, which can achieve the effect that two different reactions may be catalyzed by the same ionic liquid. The present invention employs a simple catalyst system, and achieves the efficient separation of the catalyst, the byproduct water, the product and the reaction materials in a separation manner combining the extraction and the rectification.

19 Claims, 2 Drawing Sheets

(56) References Cited

U.S. PATENT DOCUMENTS

| | | |
|---|---|---|
| 8,344,183 B2 | 1/2013 | Chen et al. |
| 2007/0135649 A1 | 6/2007 | Xia et al. |
| 2007/0260094 A1 | 11/2007 | Schelling et al. |
| 2008/0207954 A1 | 8/2008 | Stroefer et al. |
| 2008/0207955 A1 | 8/2008 | Stroefer et al. |
| 2008/0293954 A1 | 11/2008 | Chen et al. |
| 2010/0270140 A1 | 10/2010 | Siegert et al. |
| 2011/0288343 A1 | 11/2011 | Chen et al. |
| 2011/0313202 A1 | 12/2011 | Xia et al. |
| 2014/0114092 A1* | 4/2014 | Xia et al. ............ 568/601 |
| 2014/0114093 A1 | 4/2014 | Chen et al. |
| 2015/0094497 A1* | 4/2015 | Chen et al. ............ 568/679 |

FOREIGN PATENT DOCUMENTS

| | | |
|---|---|---|
| CN | 102701923 A | 10/2012 |
| EP | 1505049 A1 | 2/2005 |
| GB | 2483325 A | 3/2012 |
| GB | 2489534 A | 10/2012 |
| WO | WO 2006/045506 A1 | 5/2006 |
| WO | WO 2012/046169 A1 | 4/2012 |

\* cited by examiner

SYSTEM AND METHOD FOR CONTINUOUSLY PRODUCING POLYOXYMETHYLENE DIMETHYL ETHERS

CROSS-REFERENCE AND RELATED APPLICATION

This application claims priority on Chinese patent application no. 201210397887.3 filed on Oct. 18, 2012. The contents and subject matter of the priority application is incorporated herein by reference.

FIELD OF THE INVENTION

The present invention relates to a novel system and method for continuously producing polyoxymethylene dimethyl ethers, particularly, system and process for continuously producing polyoxymethylene dimethyl ethers from formaldehyde via trioxymethylene.

BACKGROUND OF THE INVENTION

The middle part of polyoxymethylene dimethyl ethers ($CH_3O(CH_2O)_nCH_3$, $DMM_n$, n=2-8) is formaldehyde oligomer, while the both ends thereof are terminated with methyl. The $DMM_n$ with n≤5 has excellent solubilizing power and great permeating ability. It is miscible with water and many organic solvents, and may be widely used as industry solvents, pigment dispersant, and so on. $DMM_n$ is also an oxygen-containing blending component for diesel oil with great potential, which have very high cetane number ($DMM_2$: 63, $DMM_3$: 78, $DMM_4$: 90, $DMM_5$: 100) and oxygen content (42%-49%). When added to the diesel oil at 10%-20 v/v %, it is possible to significantly improve the combustion characteristic of the diesel oil, effectively increase the thermal efficiency, and greatly reduce the emission of NO and soot. U.S. Pat. No. 7,235,113 discloses that when 15 v/v % of $DMM_{3-6}$ is added into the diesel oil, the emission of $NO_x$, particles, and hydrocarbon of the exhaust achieves Euro V standard.

The traditional synthesis process of $DMM_n$ is the production through the acetalation reaction between a compound providing formaldehyde oligomer and a compound providing methyl for terminating in the presence of an acidic catalyst. Since 2001, Snamprogetti S.P.A. (EP 1505049 A1, U.S. Pat. No. 6,534,685), BASF (WO 2006/045506 A1, CA 2581502 A1, U.S. Patent Application Publication 20070260094 A1) and other companies disclose processes for continuously producing $DMM_n$ from polyformaldehyde or trioxymethylene and methanol by employing liquid acid such as $H_2SO_4$ or $CF_3SO_3H$ as the catalyst. After the reaction is completed, the catalyst and the byproduct water are removed from the reaction liquid through the absorption with a silica gel or a resin. The unreacted reaction materials, the light component ($DMM_{1-2}$), the product ($DMM_{3-5}$) and the heavy component ($DMM_{≥5}$) are separated by employing a two-stage rectification process. The reaction materials, the light component and the heavy component are recycled to the reactor for reuse. The above reaction solution separation process employs large amount of absorbents, thereby resulting in a large energy consumption of the treatment, and the catalyst cannot be reused via recycling. Furthermore, the above process use trioxymethylene as reaction material and thus is costly.

U.S. Patent Application Publication 20080207954 A1 by BASF Corporation discloses a process of producing $DMM_{1-5}$ through the reaction of methanol and formaldehyde in an aqueous solution catalyzed by a liquid acid or a solid acid, wherein a reaction rectification technique is employed and then via a multi-stage rectification process to separate the light components ($DMM_{1-2}$ and unreacted raw materials), the product $DMM_{3-4}$ (containing water) and the heavy components $DMM_{>4}$ from the rectification column top reaction liquid ($DMM_{1-5}$, unreacted raw materials, and water). The crude products from which $DMM_{3-4}$, the light components, and the heavy components are separated by phase separation technology are recycled to the reaction unit for reuse. But in the actual operation of the process, it is difficult to separate methanol, water, and $DMM_n$ due to azeotrope, Meanwhile, the good miscibility of methanol, water and $DMM_{3-4}$ causes phase separation more difficult.

Recently, Lanzhou Institute of Chemical Physics, Chinese Academy of Sciences, as in U.S. patent application Ser. No. 13/154,359 and published as U.S. Patent Application Publication No. 20110288343 A1 and U.S. patent application Ser. No. 13/164,677 and published as U.S. Patent Application Publication No. 20110313202 A1, discloses a method of synthesizing $DMM_n$ through the reaction of trioxymethylene and methanol catalyzed by an ionic liquid, wherein the reaction solution is sequentially subjected to flash evaporation, film separation, and phase separation, to separate the light components ($DMM_{1-2}$, a part of water, unreacted raw material), crude products $DMM_{3-8}$, and catalyst. In order to achieve the purification of the products $DMM_{3-8}$, small amount of water and catalyst contained in the crude products need to be removed by absorbed with silica gel or anion exchange resins, thus, the recovery rate of catalyst of the process is relatively low.

SUMMARY OF THE INVENTION

The object of the present invention is to provide a method for continuously producing polyoxymethylene dimethyl ethers from formaldehyde via trioxymethylene, to overcome the disadvantages of the prior art.

The process of the present invention produces polyoxymethylene dimethyl ethers via continues polymerization and acetalation reaction by employing an acid ionic liquid as a catalyst, and an aqueous formaldehyde solution as an initial reaction material, wherein the polyoxymethylene dimethyl ethers are represented as $DMM_n$, n is an integer ranging from 1 to 8.

In a first aspect, the present invention provides a system for continuously producing polyoxymethylene dimethyl ethers (hereinafter, is also simply described as "The system of the present invention"), comprising:

a polymerization reaction unit, comprising a polymerization reactor, an extraction column and a rectification column; wherein a polymerization reaction takes place in the presence of the first acid ionic liquid as a catalyst by using formaldehyde as a reaction material in the polymerization reactor, the gas generated in the polymer reactor enters the extraction column after condensation, followed by the extraction with an extractant, and trioxymethylene is obtained through the rectification in the rectification column;

an acetalation unit, comprising a single or multi-stage reactor and a gas phase condenser; wherein in the single or multi-stage reactor, the trioxymethylene obtained in the polymerization reaction unit is subjected to an acetalation reaction with methanol in the presence of a second acid ionic liquid catalyst resulting in crude polyoxymethylene dimethyl ethers ($DMM_n$, n=1-8);

a product separation unit, comprising an extraction column and a single or multi-stage rectification column connected to each other in series; wherein the crude $DMM_n$ is separated into a light phase and a heavy phase in the product separation unit, wherein the heavy phase contains a second ionic liquid catalyst and water, the light phase contains unreacted methanol and $DMM_1$, trioxymethylene and $DMM_2$, $DMM_{3-8}$, and the extractant; and a catalyst regeneration unit, comprising a film separator; wherein the catalyst regeneration unit receives the heavy phase separated from the product separation system, and the catalyst in the heavy phase is recycled to the acetalation reaction unit after dehydration.

In one embodiment of the system of the present invention, the rectification columns used in the polymerization reaction unit and the product separation unit are tray columns or packed columns having a plate number of 3-10.

In one preferred embodiment of the reaction system of the present invention, the material of the reactor may be chosen as 316L stainless steel.

In one preferred embodiment of the reaction system of the present invention, the polymerization reactor includes a reactor, a reactive rectification column and a gas phase condenser. In such case, a feasible configuration is: the gas outlet of the reactor is interconnected with the gas inlet of the reactive rectification column via pipe-line, the gas outlet of the reactive rectification column is interconnected with the inlet of the gas phase condenser via pipe-line, the liquid outlet on the bottom of the reactive rectification column is interconnected with the liquid reflow inlet of the reactor via pipe-line, the outlet of the gas phase condenser is interconnected with the inlet of the extraction column via pipe-line, and the light phase outlet of the extraction column is interconnected with the inlet of the rectification column via pipe-line.

In one preferred embodiment of the reaction system of the present invention, the outlet of the single or multi-stage reactor in the acetalation unit is interconnected with the inlet of the gas phase condenser in the acetalation unit via pipe-line.

In one preferred embodiment of the reaction system of the present invention, the rectification columns includes a light component rectification column, an extractant rectification column and a product rectification column. In such case, a feasible configuration is: the reaction solution inlet of the extraction column is interconnected with the outlet of the gas phase condenser in the acetalation unit via pipe-line, the light phase outlet of the extraction column is interconnected with the inlet of the light component rectification column via pipe-line, the heavy phase outlet of the extraction column is interconnected with the inlet of the film separator via pipe-line, the liquid outlet of the light component rectification column is interconnected with the inlet of the extractant rectification column via pipe-line, the liquid outlet of the extractant rectification column is interconnected with the inlet of the product rectification column via pipe-line, the gas outlets of the light component rectification column and product rectification column are interconnected with the inlet of acetalation reactor via pipe-lines.

In one embodiment of the system of the present invention, the film separator is selected from a falling film evaporator, a wiped thin film evaporator or a thin film evaporator. In one preferred embodiment, the configuration of the film separator is: the heavy phase outlet thereof is interconnected with the inlet of the catalyst reservoir via pipe-line.

In a second aspect, the present invention provides a method for continuously producing polyoxymethylene dimethyl ethers (hereinafter, is also simply described as "the method of the invention"), comprising the following steps:

1) continuously conducting polymerization reaction at about 80-120° C. under a slightly negative pressure or the normal pressure by using about 45-70 wt. % aqueous formaldehyde solution as a reaction material in the presence of a first acid ionic liquid IL I as a catalyst, resulting in a trioxymethylene synthesized solution which is then subjected to an extraction with an extractant, followed by rectification, thereby obtaining the trioxymethylene;

2) subjecting the trioxymethylene from step 1) and methanol to continuous acetalation reaction at about 100-130° C., about 0.5-5.0 Mpa in the presence of a second acid ionic liquid IL II as a catalyst, resulting in a reaction effluent containing the produced $DMM_{1-8}$ and water, as well as the unreacted reaction raw materials and the catalyst;

3) extracting a light phase and a heavy phase from the reaction effluent obtained in step 2) using an extractant, wherein the light phase contains the extractant, $DMM_{1-8}$, the unreacted trioxymethylene and a part of the methanol, while the heavy phase contains an aqueous catalyst solution;

4) separating most of the water from the aqueous catalyst solution from step 3) by evaporation, and the recovered catalyst is returned to step 2) for reuse.

In the method of the invention, the first acid ionic liquids IL I and the second acid ionic liquids IL II may be the same or different, and the cation moiety of each of them are independently selected from one of a quaternary ammonium cation, a quaternary phosphinium cation, an imidazolium cation, a pyridinium cation, and other heterocyclic cations, while the anion moiety of each of them are independently selected from one of a p-toluene sulphonate, a trifluoromethyl sulphonate, a methyl sulphonate, bisulfate and a trifluoroacetate.

In one preferred embodiment of the method of the invention, the total amount of the acid ionic liquid catalyst is about 1-5 wt. % of the total reaction materials.

In another preferred embodiment of the method of the invention, the extractant used in step 1) is one or more extractant(s) selected from n-hexane, cyclohexane, petroleum ether, chloroform, benzene, toluene, xylene, or ethyl acetate, preferably cyclohexane, benzene, or toluene.

In one preferred embodiment of the method of the invention, the amount of the extractant used in step 1) is 1-3 times more than the volume of the reaction solution.

In one preferred embodiment of the method of the invention, the molar ratio of the trioxymethylene to the methanol in step 2) is about 0.3-1.0.

In another preferred embodiment of the method of the invention, the reaction in step 2) is processed under the protection of nitrogen.

In one preferred embodiment of the method of the invention, the reaction pressure in step 2) is about 2.0-3.0 Mpa, and the reaction residence time is about 30-60 min.

In another preferred embodiment of the method of the invention, the catalyst in step 2) accounts for about 1-5 wt. % of all the reaction materials.

In one preferred embodiment of the method of the invention, the extractant used in step 3) is one or more extractant(s) selected from n-hexane, cyclohexane, petroleum ether, chloroform, benzene, toluene, xylene, or ethyl acetate, preferably cyclohexane, benzene, or toluene.

In another preferred embodiment of the method of the invention, the amount of the extractant used in step 3) is 1-3 times more than the volume of the reaction solution.

In one preferred embodiment of the method of the invention, the extraction temperature in step 3) is about 30-40° C.

In one preferred embodiment of the method of the invention, the evaporating temperature in step 4) is about 40-60° C., and the vacuum degree is about −0.08 to −0.09 MPa.

It should be noticed that, the above process parameters and the reaction materials such as feedstocks, extractants, and catalysts, and the like used in the method of the invention may also be applied to the system of the present invention.

The present invention provides the following advantages:

first, the present invention produces polyoxymethylene dimethyl ethers through continuous polymerization and acetalation reaction by employing an aqueous formaldehyde solution as a initial reaction material, wherein the reaction materials is cheap and easily available;

second, both of the polymerization and acetalation reaction of the present invention employ the ionic liquid as the catalyst, which achieves the effect that two different reactions may be catalyzed by one same ionic liquid, and the catalyst system is easy;

third, the corrodibility of the catalyst is low; the material of the reactor may employ 316L stainless steel; the cost of the equipments is low; both of the polymerization and the acetalation reaction have achieved the recycle of the catalyst, which further reduces the cost;

fourth, the formaldehyde polymerization reaction unit employs the reaction-rectification technology, which greatly improves the efficiency of the reaction, and achieves the integration process of the reaction and the separation; and fifth, the separation of the byproduct water, $DMM_n$, and the reaction materials of the acetalation reaction is achieved, and the azeotrope of water, $DMM_n$, methanol, and formaldehyde is destroyed, efficiently achieving the separation of the product.

BRIEF DESCRIPTION OF THE DRAWINGS

Figures are only used for describing the schematic process flow of the technical solution of the present invention, where only the necessary devices for explaining the process are drawn. For simplicity and clarity, the other necessary devices are omitted, such as meters, gas bus devices, pumps, valves, and intermediate tanks, and the like.

DETAILED DESCRIPTION OF THE INVENTION

The technical process of the invention is illustrated in association with the devices used in the method of the present invention as following (hereinafter, A, B, C, and D zones correspond to the zones noted by the reference signs A, B, C, and D in FIG. 1, respectively):

A. In the polymerization reaction zone A (corresponding to "the polymerization reaction unit" in the system of the present invention), a polymerization reaction is continuously conducted at about 80-120° C., slightly negative pressure or normal pressure (preferably from about −1.0 to 0.1 MPa), using about 45-70 wt. % aqueous formaldehyde solution as a reaction material and an acid ionic liquid IL I as a catalyst (corresponding to "the first acid ionic liquid catalyst" used in the reaction system of the present invention), resulting in trioxymethylene. The gas produced in the polymerization reaction zone is the azeotrope of trioxymethylene, formaldehyde, and water, which contains about 30-40 wt. % of trioxymethylene and about 10-30 wt. % of formaldehyde; after the combination of the gas, it enters into the gas phase condenser, and enters into the extraction column after condensation. The trioxymethylene is extracted by an extractant. The mixed liquid of the extractant and the trioxymethylene continuously flows into the rectification column, and the heavy phase from the rectification column returns to the acetalation unit; the extractant is distilled from the top of the rectification column, and recycled to the extraction column for reuse; the trioxymethylene continuously enters into the acetalation reactor from the bottom thereof.

B. In the acetalation reaction zone B (corresponding to the "acetalation unit" in the system of the invention), in a single or multi-stage reactor, the trioxymethylene from the polymerization reaction zone and methanol are subjected to continuous acetalation reaction at about 100-130° C., about 0.5-5.0 Mpa by using an acid ionic liquid IL II as the catalyst (corresponding to "the second acid ionic liquid catalyst" used in the system of the present invention); in addition to the produced $DMM_{1-8}$ and water, the reactor effluent continuously flowed out also contains the above unreacted materials and the catalyst.

C. In the product separation zone C (corresponds to the "product separation unit" in the system of the invention), the reactor effluent flowed out from the above acetalation reaction zone is lowered in pressure, continuously flows into the extraction column where $DMM_n$ and the most of reaction materials are extracted by an extractant. The extract liquor which is the product phase continuously flows from the top of the column into the rectification unit, where the recycling materials, the extractant and the product $DMM_{3-8}$ are separated; The heavy phase which is the aqueous catalyst solution continuously flows from the bottom of the column into the catalyst regeneration zone.

D. In the catalyst regeneration zone D (corresponding to the "catalyst regeneration unit" in the system of the invention), the aqueous catalyst solution from the product separation zone is continuously fed into a film separator, where most of the water is separated, and the catalyst continuously returns to the acetalation reaction zone for reuse.

The technical process of the method of the invention is specifically described below. The reaction formulas employed in the method of the invention are presented as follows: In the polymerization reaction unit, trioxymethylene is formed through formaldehyde polymerization reaction:

In the acetalation unit, $DMM_n$ is produced through acetalation reaction:

wherein in the above reaction formula, n is an integer ranging from 1 to 8, IL represents an acid ionic liquid catalyst.

As for the acid ionic liquid catalyst, it may be chosen with reference to the following preferred examples.

The structure of the examples of the quaternary ammonium cation of the acid ionic liquid catalyst employed in the present invention may be:

wherein: n and m are integer ranging from 1-15; R, $R_1$, and $R_2$ are linear alkanes having a carbon number of 1-6 or benzene rings; X is —$SO_3H$ or —COOH.

The structure of the examples of the quaternary phosphinium cation of the acid ionic liquid catalyst employed in the present invention may be:

wherein: n and m are integer ranging from 1-15; R, $R_1$, and $R_2$ are linear alkanes having a carbon number of 1-6 or benzene rings; X is —$SO_3H$ or —COOH.

The structure of the examples of the imidazolium cation of the acid ionic liquid catalyst employed in the present invention may be:

wherein: n and m are integer ranging from 1-15; R is a linear alkane having a carbon number of 1-6 or a benzene ring; X is —$SO_3H$ or —COOH.

The structure of the examples of the pyridinium cation of the acid ionic liquid catalyst employed in the present invention may be:

wherein: n and m are integer ranging from 1-15; R is a linear alkane having a carbon number of 1-6 or a benzene ring; X is —$SO_3H$ or —COOH.

The structure of the examples of the heterocyclic cation of the acid ionic liquid catalyst employed in the present invention may be:

wherein: n and m are integer ranging from 1-15; R is a linear alkane having a carbon number of 1-6 or a benzene ring; X is —$SO_3H$ or —COOH.

Examples of the anion of the acid ionic liquid catalyst employed in the present invention may include:

$CH_3PhSO_3^-, CF_3SO_3^-, CH_3SO_3^-, HSO_4^-, CF_3COO^-,$

It should be noticed here that, unless otherwise specified, all of the pressures used herein represent gauge pressure; furthermore, the description of the following process may relates to devices not shown in the figures, as stated above, these devices are only omitted for the reason of simplicity and ease of describing and illustrating the main configuration of the system of the present invention, instead of indicating that these devices are absent or unnecessary.

In addition, it should be understood that, the following description and examples are only the preferred embodiments for illustrating the present invention, which is not intended to limit the scope of the present invention, therefore the devices used in the system of the present invention do not only limited to the specific devices mentioned below, Without further elaboration, it is believed that one skilled in the art can choose the suitable devices with the similar function according to the specific situation based on the teaching of the present invention.

The process flow of the method of the invention is described below in associated with the specific configuration of the process devices shown in FIG. 1 and the flow direction of the material streams shown in FIG. 2.

(1) When the reaction starts or the catalyst is supplemented, the ionic liquid catalyst IL I is fed into a reactor R1 (corresponding to the polymerization reactor of the system of the present invention) via pipe-line 3 by a pump; the catalyst IL II is fed into a reactor R2 (corresponding to the single or multi-stage reactor of the system of the present invention) via pipe-line 17 by a pump;

(2) Formaldehyde polymerization reaction: the pressure of the whole reaction system is set at a slightly negative pressure or normal pressure, preferably from −1.0 to 0.1 MPa. The reaction material concentrated formaldehyde in the reservoir V2 continuously is metered into the formaldehyde polymerization reactor R1 via pipe-line 2, subjected to the polymerization reaction catalyzed by an ionic liquid IL I so as to produce trioxymethylene. The effluent stream from the bottom of the reactor R1 is transferred through pipe-line 6, by means of pump P1, and into a reboiler V5, then returned to the reactor R1 through pipe-line 7. The reactor is in flow communication with the reboiler, and the reaction solution is recycled between the reactor and the heat exchanger. The gas in the reactor enters from the top of the reactor R1 into a rectification column V4 via pipe-line 4, and is subjected to the gas-liquid separation in the rectification column V4. The azeotrope of trioxymethylene, formaldehyde and water is combined on the top of the rectification column and then enters into a gas phase condenser V6 via pipe-line 8. After condensation, it enters a extraction column V7 via pipe-line 9; the liquid is combined at the bottom of the rectification column and then returned to the reactor R1 via pipe-line 5.

(3) Trioxymethylene separation: the effluent of the heat exchanger V6 is fed into the extraction column V7 via pipe-line 9. The extractant is fed into the extraction column V7 from the reservoir V1 via pipe-line 10, the reaction solution is conversely and sufficiently contacted by the extractant. The extract liquor (containing trioxymethylene and extractant as the main components, and further containing a small amount of formaldehyde and methanol) continuously enters a rectification column V8 from the top via pipe-line 11, the heavy phase (formaldehyde, methanol, and water) continuously enters into a dilute formaldehyde removal unit from the bottom via pipe-line 12, and condensed into aqueous concentrated aldehyde solution which enters into the reaction materials reservoir V2. The light phase is rectificated in the rectification column V8. The extractant continuously distilled from the top returns to the extractant reservoir V1 via pipe-line 13 for reuse; the bottom liquid (trioxymethylene) continuously enters the acetalation reactor R2 via pipe-line 14.

(4) Acetalation reaction: the whole system is purged with $N_2$. The oxygen content detected by the discharged exhaust gas detecting system is lower than 10 ppm. The reaction material trioxymethylene (via pipe-line 14), methanol (via pipe-line 15), the recycled materials (via pipe-line 18), and the recycled catalyst (via pipe-line 17) continuously flow into the acetalation reactor R2 through liquid mass velocity meter (not shown in the figure), respectively. $N_2$ is purified through a purification unit, and metered into the reactor R2 via pipe-line 21. The acetalation reaction occurs at certain temperature and pressure. The effluent stream from the bottom of the reactor R2 is transferred though pipe-line 19, by means of pump P2, and into a heat exchanger V12, then returned to the reactor R2 through pipe-line 20. The reactor is in liquid communication with the heat exchanger, and the reaction solution is circulated between the reactor and the heat exchanger. The overhead stream from the reactor R2 comprises the catalyst, $DMM_{1-8}$, water, unreacted methanol and trioxymethylene.

(5) $DMM_n$ extraction separation: the effluent of the reactor R2 is fed into a heat exchanger V13 via pipe-line 22, followed by cooling down and lowering the pressure in a depressurizer V14, and is fed into an extraction column V15 via pipe-line 23. The extractant is supplied from the reservoir V1 via pipe-line 24, and into an extraction column V15, where the reaction solution is conversely and sufficiently contacted with the extractant. The extracted liquid (product phase) continuously enters a rectification column V17 from the top via pipe-line 25, and the heavy phase (the aqueous catalyst solution) continuously enters a film evaporator V16 from the bottom via pipe-line 26.

(6) $DMM_n$ rectification separation: the composition of the product phase is $DMM_{1-8}$, the extractant, unreacted methanol and the trioxymethylene. The light components (mainly containing methanol and $DMM_1$) are rectificated in the rectification column V17, continuously distilled from the top, cooled via pipe-line 28, and returned to the reaction system. The bottom liquid is fed into a rectification column V18 via pipe-line 29. The extractant is distilled from the top and returned to the extractant reservoir V1 via pipe-line 30 for reuse. The bottom liquid enters into a rectification column V19 via pipe-line 31. $DMM_2$ and trioxymethylene distilled from the top returns to the reaction unit via pipe-line 32 for reuse, and the bottom effluent (products $DMM_{3-8}$) enters a product reservoir V20 via pipe-line 33.

(7) Catalyst dehydration: the aqueous catalyst solution is continuously fed from the bottom of the extraction column V15 via pipe-line 26 into a film evaporator V16. Flash distillation is conducted at from about 40° C. to 60° C. and pressure at from about −0.08 MPa to −0.09 MPa for dehydrating, and the catalyst is recycled to a catalyst storage tank V11 via pipe-line 27.

The specific production examples are provided as following. The present invention is further described with reference to the configuration of FIG. 1 and in associated with the examples. The flow direction of the materials streams in the whole technical process is shown in FIG. 2.

EXAMPLE

The catalysts used in the following examples are shown as following:

Example 1

Figure 1:
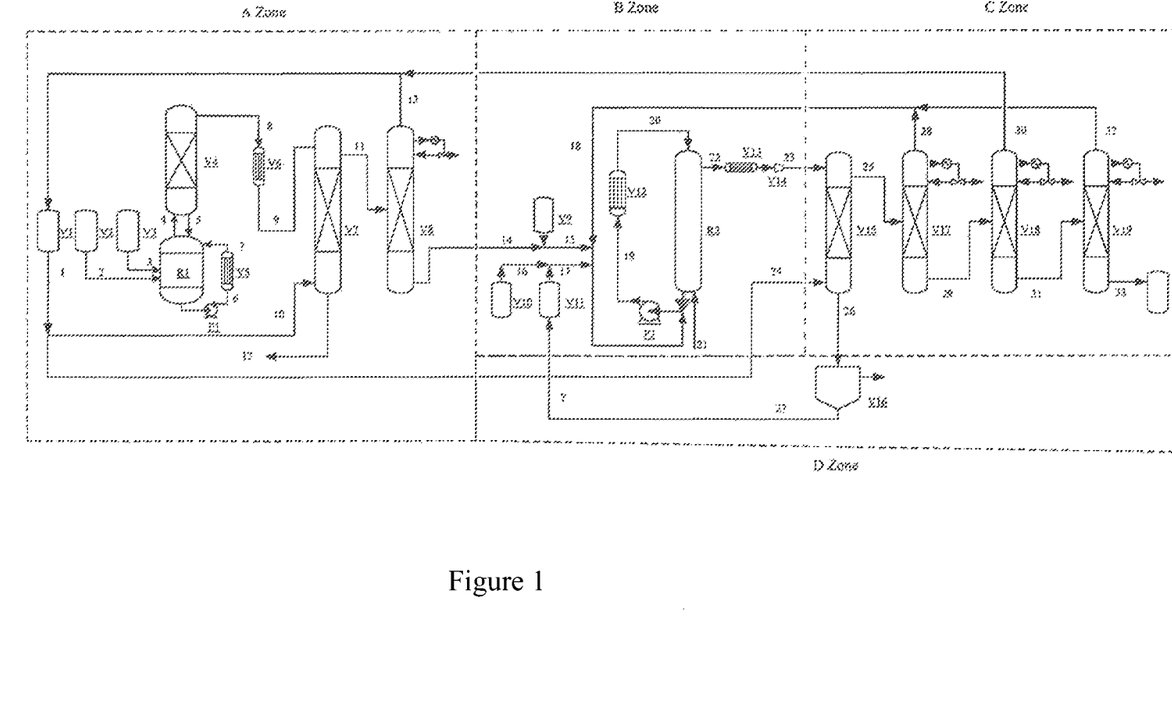
FIG. 1 is a schematic diagram showing the device configuration and process flow of one preferred aspect of the system according to the present invention.
Figure 2:
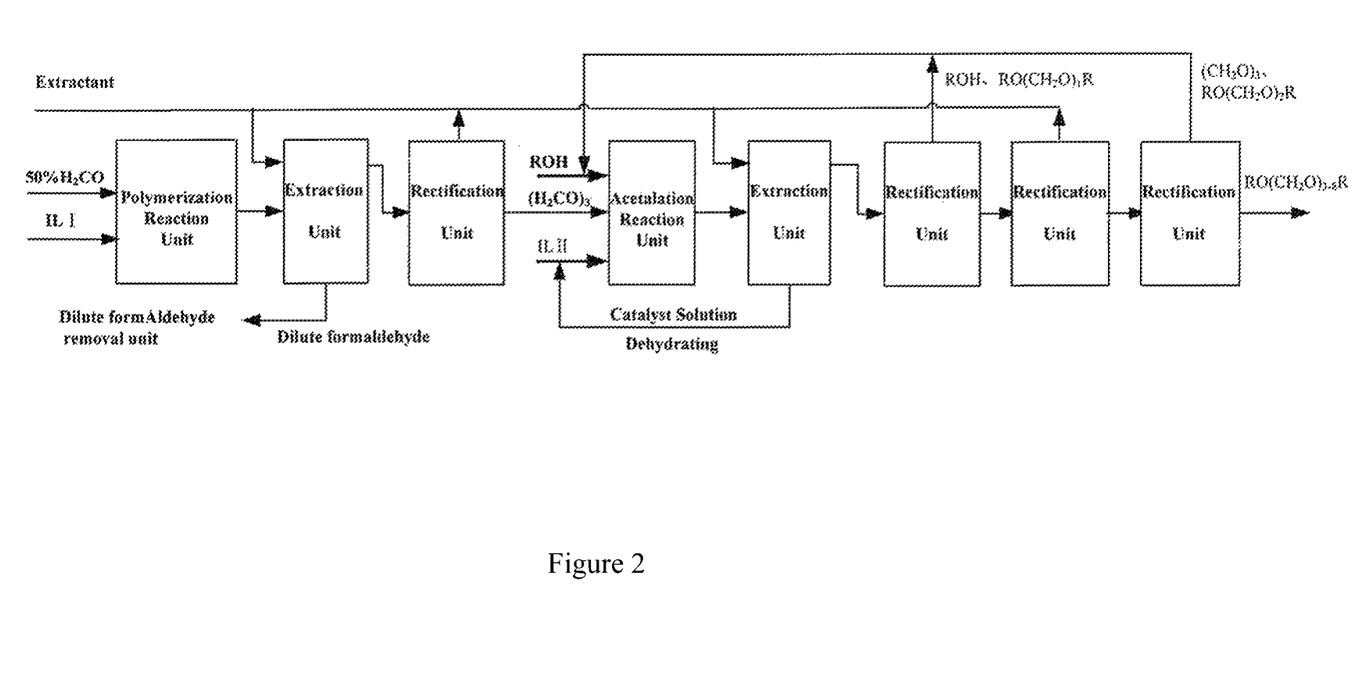
FIG. 2 is a flow chart showing the flow direction of the reaction material streams in an embodiment of the method according to the present invention.

In the reaction process shown in FIG. 1, the volume of the reactor R1 is 8 L. The reactor R1 is in flow communication with the reaction reboiler, and the reaction solution is recycled in the reactor and the heat exchanger. The reactor R2 is a tubular reactor with a volume of 500 mL.

The system was purged with high-purity nitrogen to replace air. 140 g of ionic liquid catalyst ILI-1 was continuously added into the reactor R1 for 8 h, and the amount of the catalyst used was 2.0 wt. % of the total charge amount; at the same time, aqueous formaldehyde solution with a concentration of 50 wt. % was added at a feed rate of 800 mL/h. The reaction temperature of the reactor R1 was controlled at 98-100° C. The reaction pressure was −0.05-0.05 Mpa. Trioxymethylene was formed through the polymerization of formaldehyde. The gas in the reactor entered into the rectification column. A azeotrope of trioxymethylene, formaldehyde and water was distilled off from the top at a column top temperature of 92-96° C., and entered the extraction column V7 after condensation. The extractant benzene entered into V7 from the bottom at a feed rate of 1600 mL/h (which was twice as the volume of the synthesized liquid). The heavy phase from the bottom continuously flowed into the dilute formaldehyde removal unit for recycling. The extracted liquid (product phase) from the top continuously entered into the rectification column V8. The light component benzene was continuously distilled from the top at 78-80° C. and returned to the reservoir V1 for reuse. The heavy phase trioxymethylene continuously flowed into the acetalation reactor R2.

Ionic liquid catalyst IL II-1 was added into the reactor R2 at a feed rate of 20 g/h. The feeding was stopped until the catalyst begins to be circulated, so that the concentration of the catalyst was ensured to be not less than 4 wt. %. The initial feed rate of trioxymethylene and methanol were set at 220 mL/h and 260 mL/h, respectively. The molar ratio of the trioxymethylene to the formaldehyde was 0.45. Upon the reaction materials started to be recycled, the feed rate of trioxymethylene and methanol were set at 130 mL/h and 112 mL/h, respectively. The operation condition of the reactor R2 is controlled at 115-120° C. and 2.0-3.0 MPa. The reactor effluent was fed into the extraction column V15. The feed rate of the extractant benzene was set at 1000 mL/h (which was twice of the volume of the reaction liquid). The heavy phase (the aqueous catalyst solution) from the bottom continuously entered the film evaporator V16, dehydrated at 60° C./−0.08 MPa. The catalyst returned to the reactor for reuse. The light phase (product phase) from the top continuously entered into the rectification column V17. The light components $DMM_1$, formaldehyde and methanol are continuously distilled from the top at 40-65° C., and directly returned to the reaction unit for reuse. The bottom liquids were fed into the rectification column V18. The extractant benzene was distilled at 78-80° C. from the top and returned to the reservoir V1 for reuse; the bottom liquid entered into the rectification column V19. $DMM_2$ and trioxymethylene were distilled at 98-110° C. from the top and returned to the reaction unit for reuse. The bottom effluent $DMM_{3-8}$ entered into the product reservoir.

The reaction solution, the extraction liquid, the aqueous catalyst solution, the recycled materials, and the products were sampled at regular time and the samples were quantitatively analyzed with a gas chromatograph. The acetalation reaction continues for 100 h. The averages of the experiment results are shown in Table 1.

TABLE 1

| The pipe-line where the sampling point is located | Discharging speed mL/h | Products distribution (%) |||||||||||
|---|---|---|---|---|---|---|---|---|---|---|---|---|
| | | benzene | formal-dehyde | formal-dehyde | trioxy-methylene | water | \multicolumn{7}{c}{$DMM_n$, n =} |
| | | | | | | | 1 | 2 | 3 | 4 | 5 | 6 | 7 | 8 |
| 9 | 800 | 0 | 1.1 | 19.1 | 30.0 | 49.8 | 0 | 0 | 0 | 0 | 0 | 0 | 0 | 0 |
| 14 | 220 | 0.2 | 0 | 0.4 | 98.8 | 0.6 | 0 | 0 | 0 | 0 | 0 | 0 | 0 | 0 |
| 23 | 488 | 0 | 2.5 | 0.2 | 1.2 | 6.5 | 24.2 | 20.5 | 20.9 | 14.1 | 7.3 | 2.2 | 0.4 | 0 |
| 25 | 1433 | 67.0 | 0.8 | 0.1 | 0.4 | 0.1 | 8.4 | 7.3 | 7.4 | 4.8 | 2.6 | 0.8 | 0.1 | 0 |
| 26 | 55 | 2.0 | 1.7 | 0 | 0 | 57.6 | 2.1 | 0.2 | 0 | 0 | 0 | 0 | 0 | 0 |
| 28 | 148 | 0.2 | 8.7 | 0.2 | 0 | 0 | 90.7 | 0.1 | 0 | 0 | 0 | 0 | 0 | 0 |
| 32 | 90 | 0.1 | 0 | 0 | 5.5 | 0.05 | 0 | 94.2 | 0.1 | 0 | 0 | 0 | 0 | 0 |
| 33 | 195 | 0 | 0 | 0 | 0 | 0 | 0 | 0.2 | 46.3 | 31.4 | 16.3 | 4.9 | 0.9 | 0 |

Note:
The extracted aqueous catalyst solution (26) contains catalyst in 36.4%.

Example 2

The basic process steps and the configuration of the devices were the same as Example 1, except that R2 were two overflow tanks in series in which mechanical mixing is performed. Ionic liquid IL I-2 was added into reactor R1 as the catalyst, while ionic liquid IL II-2 was added into reactor R2 as the catalyst. The operation was continued for 100 hours. The averages of the experiment results are listed in Table 2.

TABLE 2

| The pipe-line where the sampling point is located | Discharging speed mL/h | Products distribution (%) |||||||||||
|---|---|---|---|---|---|---|---|---|---|---|---|---|
| | | benzene | formal-dehyde | formal-dehyde | trioxy-methylene | water | \multicolumn{7}{c}{$DMM_n$, n =} |
| | | | | | | | 1 | 2 | 3 | 4 | 5 | 6 | 7 | 8 |
| 9 | 800 | 0 | 1.1 | 19.1 | 30.0 | 49.8 | 0 | 0 | 0 | 0 | 0 | 0 | 0 | 0 |
| 14 | 220 | 0.2 | 0 | 0.4 | 98.8 | 0.6 | 0 | 0 | 0 | 0 | 0 | 0 | 0 | 0 |
| 23 | 488 | 0 | 2.2 | 0.3 | 1.5 | 6.2 | 23.8 | 21.2 | 21.0 | 14.7 | 6.7 | 2.1 | 0.5 | 0 |
| 25 | 1433 | 62.8 | 0.8 | 0.1 | 0.6 | 0.0 | 9.4 | 8.5 | 8.3 | 6.0 | 2.7 | 0.8 | 0.2 | 0.0 |
| 26 | 55 | 2.6 | 2.7 | 0 | 0 | 55 | 3.1 | 0.2 | 0 | 0 | 0 | 0 | 0 | 0 |
| 28 | 150 | 0.3 | 7.4 | 0.8 | 0 | 0.05 | 91.4 | 0.1 | 0 | 0 | 0 | 0 | 0 | 0 |
| 32 | 83 | 0.1 | 0 | 0 | 6.7 | 0.05 | 0 | 93.1 | 0 | 0 | 0 | 0 | 0 | 0 |
| 33 | 200 | 0 | 0 | 0 | 0 | 0 | 0 | 0.3 | 46.4 | 32.7 | 14.9 | 4.7 | 1.1 | 0.0 |

Note:
The extracted aqueous catalyst solution (26) contains catalyst in 36.4%.

Example 3

The basic process steps and the configuration of the devices as well as the parameters thereof were the same as Example 1, except that toluene was used as the extractant. The reaction ran continuously for 100 hours, resulting in 199.0 mL/h $DMM_{3-8}$ product (from pipe-line 33).

Example 4

The basic process steps and the configuration of the devices as well as the parameters thereof were the same as Example 1, except that the amount of the extractant was one time more than the volume of the reaction liquid. The reaction ran continuously for 100 hours, resulting in 191.2 mL/h $DMM_{3-8}$ product (from pipe-line 33).

Example 5

The basic process steps and the configuration of the devices as well as the parameters thereof were the same as Example 1, except that the molar ratio of the trioxymethylene to the methanol was 0.6:1. The reaction ran continuously for 100 hours, resulting in 207.2 mL/h $DMM_{3-8}$ product (from pipe-line 33).

Example 6

The basic process steps and the configuration of the devices as well as the parameters thereof were the same as Example 1, except that the molar ratio of the trioxymethylene to the methanol was 0.3:1. The reaction ran continuously for 100 hours, resulting in 85.2 mL/h $DMM_{3-8}$ product (from pipe-line 33).

Example 7

The basic process steps and the configuration of the devices as well as the parameters thereof were the same as Example 1, except that the amount of catalyst IL II-1 was 2 wt. % of the total charge amount. The reaction ran continuously for 100 hours, resulting in 146.0 mL/h $DMM_{3-8}$ product (from pipe-line 33).

We claim:

1. A system for continuously producing polyoxymethylene dimethyl ethers, comprising:
    a polymerization reaction unit, comprising a polymerization reactor, an extraction column, and a rectification column, wherein a polymerization reaction takes place in the presence of a first acid ionic liquid as a catalyst by using formaldehyde as a reaction material in the polymerization reactor, a gas generated in the polymerization reactor enters the extraction column after condensation, followed by extraction by an extractant, and trioxymethylene is obtained through the rectification in the rectification column;
    an acetalation unit, comprising a single or multi-stage reactor and a gas phase condenser, wherein in the single or multi-stage reactor, the trioxymethylene obtained in the polymerization reaction unit is subjected to an acetalation reaction with methanol in the presence of a second acid ionic liquid catalyst resulting in crude polyoxymethylene dimethyl ethers ($DMM_n$, n=1-8);
    a product separation unit, comprising an extraction column and a single or multi-stage rectification column connected to each other in series; wherein the crude $DMM_n$ is separated into a light phase and a heavy phase in the product separation unit, wherein the heavy phase contains the second acid ionic liquid catalyst and water, the light phase contains unreacted methanol and $DMM_1$, trioxymethylene and $DMM_2$, $DMM_{3-8}$, and the extractant; and
    a catalyst regeneration unit, comprising a film separator, wherein the catalyst regeneration unit receives the heavy phase separated from the product separation unit, and the second acid ionic liquid catalyst in the heavy phase is recycled to the acetalation reaction unit after dehydration in the catalyst regeneration unit.

2. The system of claim 1, wherein the polymerization reactor in the polymerization reaction unit comprises a reactor, a reactive rectification column, and a gas phase condenser.

3. The system of claim 1, wherein the single or multi-stage reactor in the acetalation unit is a single or multi-stage tubular reactor or an overflow tank.

4. The system of claim 1, wherein the single or multi-stage rectification column in the product separation unit comprises a light component rectification column, an extractant rectification column, and a product rectification column.

5. The system of claim 1, wherein the rectification columns in the polymerization reaction unit and the product separation unit are tray columns or packed columns having a plate number of 3-10.

6. The system of claim 1, wherein the film separator in the catalyst regeneration unit is selected from a falling film evaporator, a wiped thin film evaporator, or a thin film evaporator.

7. The system of claim 1, wherein the first acid ionic liquid catalyst (IL I) has a cation moiety that is a quaternary ammonium cation, a quaternary phosphinium cation, an imidazolium cation, a pyridinium cation, or a heterocyclic cation, and an anion moiety that is a p-toluene sulphonate, a trifluoromethyl sulphonate, methyl sulphonate, bisulfate, or trifluoroacetate.

8. The system of claim 1, wherein the second acid ionic liquid catalyst (IL II) has a cation moiety that is a quaternary ammonium cation, a quaternary phosphinium cation, an imidazolium cation, a pyridinium cation, and a heterocyclic cation, and an anion moiety that is a p-toluene sulphonate, a trifluoromethyl sulphonate, methyl sulphonate, bisulfate, or trifluoroacetate.

9. The system of claim 1, wherein the first acid ionic liquid catalyst and the second acid ionic liquid catalyst are the same.

10. A method for continuously producing polyoxymethylene dimethyl ethers according to claim 1, comprising:
    1) continuously conducting polymerization reaction in the polymerization reactor at about 80-120° C. under a slightly negative pressure or the normal pressure by using about 45-70 wt. % aqueous formaldehyde solution as a reaction material in the presence of a first acid ionic liquid catalyst (IL I) as a catalyst, resulting in a trioxymethylene synthesized solution which is then subjected to extraction by an extractant in the extraction column, followed by rectification in the rectification column, thereby obtaining the trioxymethylene;
    2) subjecting the trioxymethylene from step 1) and methanol to continuous acetalation reaction in the acetalation unit at about 100-130° C., about 0.5-5.0 Mpa in the presence of a second acid ionic liquid catalyst (IL II) as a catalyst, resulting in a reaction effluent containing the produced $DMM_{1-8}$, water, unreacted materials and the catalyst;
    3) extracting in the product separation unit a light phase and a heavy phase from the reaction effluent obtained in step 2) using an extractant, wherein the light phase contains the extractant, $DMM_{1-8}$, the unreacted trioxymethylene and a part of the methanol, while the heavy phase contains an aqueous catalyst solution; and 4) separating most of the water from the aqueous catalyst solution from step 3) by evaporation in the catalyst regeneration unit, and the recovered catalyst is returned to step 2) for reuse.

11. The method of claim 10, wherein the total amount of the acid ionic liquid catalyst accounts for about 1-5 wt. % of all the reaction materials.

12. The method of claim 10, wherein the molar ratio of the trioxymethylene to the methanol in step 2) is about 0.3-1.0.

13. The method of claim 10, wherein the reaction pressure in step 2) is about 2.0-3.0 MPa, and the reaction residence time is about 30-60 min.

14. The method of claim 10, wherein the extractant is n-hexane, cyclohexane, petroleum ether, chloroform, benzene, toluene, xylene, ethyl acetate, or a mixture thereof.

15. The method of claim 10, wherein the extraction temperature in step 3) is about 30-40° C.

16. The method of claim 10, wherein the evaporating temperature in step 4) is about 40-60° C., and the vacuum degree is about −0.08 to −0.09 MPa.

17. The method of claim 10, wherein the first acid ionic liquid catalyst (IL I) has a cation moiety that is a quaternary ammonium cation, a quaternary phosphinium cation, an imidazolium cation, a pyridinium cation, or a heterocyclic cation, and an anion moiety that is a p-toluene sulphonate, a trifluoromethyl sulphonate, methyl sulphonate, bisulfate, or trifluoroacetate.

18. The method of claim 10, wherein the second acid ionic liquid catalyst (IL II) has a cation moiety that is a quaternary ammonium cation, a quaternary phosphinium cation, an imidazolium cation, a pyridinium cation, or a heterocyclic cation, and an anion moiety that is a p-toluene sulphonate, a trifluoromethyl sulphonate, methyl sulphonate, bisulfate, or trifluoroacetate.

19. The method of claim 10, wherein the first acid ionic liquid catalyst and the second acid ionic liquid catalyst are the same.

* * * * *